(12) United States Patent
Mitidieri et al.

(10) Patent No.: US 8,263,660 B2
(45) Date of Patent: Sep. 11, 2012

(54) STABLE HYPERBARIC COMPOSITION COMPRISING PRILOCAINE HCL, USE OF SAID NEW COMPOSITION FOR INTRATHECAL ANAETHESIA, AND METHOD FOR MANUFACTURING SAID COMPOSITION

(75) Inventors: Augusto Mitidieri, Morcote (CH); Elisabetta Donati, Cavallasca (IT)

(73) Assignee: Sintetica S.A., Mendrisio (CH)

( * ) Notice: Subject to any disclaimer, the term of this patent is extended or adjusted under 35 U.S.C. 154(b) by 0 days.

(21) Appl. No.: 12/279,049

(22) PCT Filed: Feb. 14, 2007

(86) PCT No.: PCT/EP2007/051442
§ 371 (c)(1),
(2), (4) Date: Aug. 11, 2008

(87) PCT Pub. No.: WO2007/093617
PCT Pub. Date: Aug. 23, 2007

(65) Prior Publication Data
US 2009/0036539 A1 Feb. 5, 2009

(30) Foreign Application Priority Data
Feb. 16, 2006 (IT) .............. MI2006A0282

(51) Int. Cl.
*A61K 31/165* (2006.01)
(52) U.S. Cl. .................................. 514/626
(58) Field of Classification Search ............. None
See application file for complete search history.

(56) References Cited

U.S. PATENT DOCUMENTS
2003/0225401 A1   12/2003   Eggers et al. ............. 606/39

OTHER PUBLICATIONS

Sumi et al (Can J Anaesth 43:1138-1143, 1996).*
International Search Report for: PCT/EP2007051442, dated Sep. 6, 2007.
Hampl Karl, et al: "Transient neurologic symptoms after spinal anesthesia. A lower incidence with prilocaine and bupivacaine than with lidocaine" Anesthesiology, vol. 88, No. 3, 1998, pp. 629-633, XP008083085 ISSN: 0143-7208 p. 629, left-hand column, paragraph 2 p. 630; table 1.
De Jong R H: The intrathecal lidocaine enigma: On the brink of Cauda equinopathy: Seminars in Anesthesia, Saunders, Co, New York, NY, US, vol. 17, No. 4,Dec. 1998, pp. 287-298, XP005457749, ISSN: 0277-0326, p. 292; table 4.
Fisher A., et al: "Spinal analgesic agents" Anaesthesia, vol. 26, No. 3, 1971, pp. 324-329, XP008083064, p. 326 paragraph 1.
Crankshaw T P: "Citanest (prilocaine) in spinal analgesia" ACTA Anaesth Scandinav, vol. XVI, 1965, pp. 287-190, XP008083072, p. 287, paragraph 1.
Eriksson E: "L 67—experimental evaluation of a new local anaesthetic in man" ACTA Anaesth Scandinav, vol. 5, 1961, pp. 191-205, XP008083180, p. 191, paragraph 1, p. 194, paragraph 3.
Makin A. et al.: "I.v. regional anaesthesia. Comparison of 0.25% prilocaine with or without 5% dextrose" British Journal O Fanaesthesia, Proceedings of the Anaesthetic Research Society, vol. 79, 1997, pp. 674P-687P, XP002449168, p. 687P, left-hand column, last paragraph—right-hand column, paragraph 1.

* cited by examiner

*Primary Examiner* — Craig Ricci
(74) *Attorney, Agent, or Firm* — Squires Sanders (US) LLP

(57) ABSTRACT

The present invention concerns new preservative-free hyperbaric compositions of prilocaine HCl intended for use in intrathecal narcosis, characterized by high stability at ambient temperature (15° C. -27° C.). The present invention also concerns a method for manufacturing said compositions.

8 Claims, No Drawings

STABLE HYPERBARIC COMPOSITION COMPRISING PRILOCAINE HCL, USE OF SAID NEW COMPOSITION FOR INTRATHECAL ANAETHESIA, AND METHOD FOR MANUFACTURING SAID COMPOSITION

FIELD OF THE INVENTION

The present invention concerns the field of intrathecal anaesthesia, and in particular the provision of new stable compositions suited to this specific type of administration.

TECHNICAL BACKGROUND

Given the current trend in medicine—dictated by the requirement of national health services and private insurance companies to limit medication costs—for carrying out the greatest possible number of operations without general anaesthetic and therefore without patient hospitalisation, there is current interest in further developing regional and local, rather than general, anaesthetic techniques. Given recent developments and the comparative progress achieved, regional and local anaesthesias prove to be even safer than general anaesthesia, which is hence avoided particularly in vulnerable patients such as the elderly. The problem therefore is not just of cost to be borne by the community, but is primarily concerned with improving the quality of therapy offered to patients.

The aforementioned so-called regional anaesthesias include, as a rule, techniques suitable for administering local anaesthetics to the spine and the nerve plexus of the upper limbs, as well as to periphery of individual nerves. Spinal techniques can be divided into epidural injection and intrathecal injection (whereby the narcotic is injected into the so-called subarachnoid space) which are both suitable for inducing, by means of a targeted anaesthetic injection into a contained spinal space, a regional anaesthesia of the lower limbs by temporarily interrupting the nervous connection between said limbs and the brain. While the intrathecal technique is more invasive than the epidural technique (in that the injection is carried out in a region deeper within the spine), it has the advantage of requiring comparatively small quantities of the anaesthetic used.

An ideal intrathecal anaesthetic for outpatient surgery use should give an immediate or at least a rapid effect (and thus have a brief onset time), should have an easily adjustable action for a predictable duration, and should exhibit low neurotoxicity as well as be without side effects.

Anaesthetics currently used for intrathecal application include lidocaine, procaine and bupivacaine, this latter being used in small doses. Unfortunately, none of the pharmacological profiles of these substances can be considered ideal. For example, news about permanent neurological damage has led to doubts suggesting the potential neurotoxicity of lidocaine (1-3). On the other hand, procaine can attain an inadequacy rate as high as 17% (4). Although bupivacaine is efficient, it can actually induce blocks whose duration in some cases is hard to predict despite the administered doses being low.

It therefore appears that none of the anaesthetics currently used for intrathecal application, in currently authorized formulations, fully satisfies all the criteria that characterize an ideal preparation. The need therefore remains to provide additional and improved compositions for intrathecal administration.

This is because a hyperbaric formulation of prilocaine authorized for intrathecal use does not currently exist.

This has not always been the case, in that a hyperbaric (thickened with glucose) 5% prilocaine solution used to be available on the English and French markets, intended for this use. This preparation actually had problems of stability over time and was withdrawn from sale because the phenomenon was never resolved. Given the obvious advantages of this active principle, other glucose-free prilocaine formulations remain available, also destined for other uses.

In view of the aforestated, the problem therefore exists of providing a stable preparation of hyperbaric prilocaine for intrathecal use, as well as a process for its preparation.

SUMMARY

With the aim of resolving the aforesaid problems, the inventors of the present patent application have now surprisingly found new pharmaceutical compositions comprising prilocaine HCl and glucose in a hyperbaric solution, characterized by having a shelf-life at ambient temperature of at least 5 years, and whose 2-methylaniline content, throughout the entire shelf-life duration, is less than 0.10% relative to the quantity of prilocaine HCl contained. The new pharmaceutical compositions in accordance with the present invention are particularly suitable for intrathecal administration.

The inventors of the present patent application have also found a method for obtaining a pharmaceutical composition as aforesaid comprising the following steps:

mixing water for injection, prilocaine HCl and anhydrous glucose in the necessary quantities, in an inert gas atmosphere to give a medicated solution under inert gas, optionally adding NaOH to the medicated solution, to stabilize the pH from 5.0 to 6.0, filtering the medicated solution through a sterilizing filter (0.22 μm), distributing the filtered medicated solution into vials under inert gas, sterilizing the medicated solution in sealed vials under inert gas at least 121° C. for at least 15 minutes, to provide a sterilized medicated solution.

DETAILED DESCRIPTION OF THE INVENTION

Prilocaine, or N-(2-methylphenyl)-o-propylamino)propanamide (CAS 1786-81-8) in its hydrochloride addition-salt form (prilocaine HCl) is a long known narcotic substance, already introduced in clinics in the 1960s. Prilocaine (HCl), in its racemic form (currently marketed as Xylonest® and Citanest® by AstraZeneca in various variants with or without preserving agents and with or without small quantities of adrenaline) is today only used in intravenous regional anaesthesia (IVRA), in concentrations of 0.5% and 1.0%, and also for epidural anaesthesia in concentrations of 1.0% and 2.0%. Within the sphere of the aforesaid administration methods, prilocaine is widely valued for its low systemic toxicity which is due to the fact that prilocaine (in contrast to lidocaine, for example, a very similar anaesthetic in terms of onset and duration of nerve blockage) is a secondary amine—a peculiarity which facilitates its metabolization. Within the sphere of epidural use, prilocaine is hence well established and is only not recommended for obstetric anaesthesia in doses above 600 mg, an amount which is considered to be linked with risk of methemoglobin formation.

Regarding intrathecal administration, however, hyperbaric prilocaine (i.e. whose density has been increased by addition of glucose) is not currently authorized in any country in the world for this specific type of administration, and therefore there are currently no formulations on the market suited to this purpose.

As aforesaid, although a prilocaine hyperbaric formulation (Citanest 5% Heavy®) for intrathecal use was indeed tested in the 1970s (5, 6), the product was then withdrawn from the market in 1978 because problems with stability, and apparently also loss of effectiveness, occurred in the preparations of that time. Although the withdrawal was criticized by some experts of the field, investigations conducted at the time did not lead to a resolution of the problems (7, 8). In an attempt to overcome the aforesaid difficulties, related among other things to the occurrence of insufficiently deep anaesthesia, experiments were then undertaken in France in the 1980s (9, 10, 11) with prilocaine and morphine mixtures, mainly with the aim of increasing the depth of resulting anaesthesia. Despite the progress made, however, said preparations were not introduced commercially. The same applies to the hyperbaric preparations of 0.5% prilocaine examined in France at the end of the 1980s (12), which by comparative studies were shown to be measurably inferior to bupivacaine in terms of percentage probable inadequacy.

In view of the aforesaid, and particularly in view of the drawbacks of known formulations, intrathecal use of prilocaine HCl in hyperbaric solution as a standard medication was no longer considered feasible after the events in 1978 which led to the disappearance of the commercial product. Despite this, interest in the use of this active principle in the intrathecal field has always remained very high as indicated by numerous clinical studies over the decades, often conducted, in the absence of commercial products, either with formulations prepared ad hoc or with unauthorized formulations. This is also confirmed in recent works (13, 14, 15, 16, 17) which seem to have now brought to light the fact that lidocaine, a widely used substance in the intrathecal field, tends to cause lower limb pain (so called transitory neurological symptoms or TNS), to a considerably greater degree than prilocaine.

It therefore appears that the need to develop new stable pharmaceutical formulations of hyperbaric prilocaine suited to intrathecal administration has been felt for some time, because of the unresolved problem arising from the withdrawal of Citanest 5% Heavy® from the market.

The present patent application therefore focuses on the problem of overcoming the aforesaid drawbacks. The inventors of the present patent application have now surprisingly found that the problems of the known art as previously described can be overcome by the provision of a new pharmaceutical composition comprising prilocaine HCl and glucose in a hyperbaric solution in water for injection, characterized by having an ambient temperature shelf-life of at least 5 years. The new hyperbaric composition found by the inventors of the present patent application is hence considered stable and is used as an injectable solution for intrathecal anaesthesia, overcoming the problems associated with old formulations, for example the formation of coloured contaminants, even after several years' storage without taking particular precautions (at ambient temperature, in clear vials). The term "ambient temperature", for the purposes of the present patent application, means a temperature between 15° C. and 27° C., preferably 25±2° C. The new stable hyperbaric composition herein described is preferably without stabilizers or preservatives and can comprise from 0.5% to 6% of prilocaine HCl. Preferably the new stable hyperbaric composition comprises from 1% to 3% (p/V) of prilocaine HCl, and even more preferably from 1.8% to 2.2% (p/V) of prilocaine HCl. Particularly preferred is a new stable hyperbaric composition comprising 2.0% (p/V) of prilocaine HCl.

The 2-methylaniline content of the new stable hyperbaric compositions of the present invention is less than 0.10%, preferably less than 0.06% relative to the quantity of prilocaine HCl contained in the new composition, throughout the entire shelf-life duration (at least 5 years), at ambient temperature. In the first two years, the content of 2-methylaniline is found to be actually less than 0.0008% relative to the quantity of prilocaine HCl contained in the new composition. In addition, throughout the entire shelf-life duration (at least 5 years), at ambient temperature, formation of coloured contaminants was not observed as is instead described for the preparations withdrawn from the market nearly 30 years ago. This also holds true in the absence of particular precautions, i.e. provision of the new stable hyperbaric compositions in non-darkened (clear) vials.

Preferably the components of the composition of the present invention are balanced to fall within the aforesaid parameters, until an osmolarity of between 490 and 540 mOsm/kg is achieved.

In accordance with another particularly preferred embodiment, the components of the composition of the present invention are balanced to fall within the aforesaid parameters, until a relative density at 37° C. of between 1.021 and 1.031 is achieved.

Preferably, the new pharmaceutical composition provided by the inventors of the present invention is produced in accordance with a new method established by the inventors and comprises the following steps:

mixing water for injection, prilocaine HCl and anhydrous glucose in the necessary quantities, in an inert gas atmosphere to give a medicated solution under inert gas, optionally adding NaOH to the medicated solution, to stabilize the pH from 5.0 to 6.0, filtering the medicated solution through a sterilizing filter (0.22 μm), distributing the filtered medicated solution into vials under inert gas, sterilizing the medicated solution in sealed vials under inert gas at least 121° C. for at least 15 minutes, to provide a sterilized medicated solution.

Preferably, in the new abovementioned method, nitrogen or rare gases are used as inert gas.

It is important to note that the solution in vials, obtained by the aforegiven method, is able to withstand a double heat sterilization with two cycles at 121° C. for 15 minutes ($F_0 15$), a condition considered to be "overkill" for microorganisms, without the 2-methylaniline content exceeding 0.10% relative to the quantity of prilocaine HCl contained in the solution. This capacity renders the product particularly safe, even from a microbiological viewpoint, maintaining excellent stability to be achieved over time.

Experimental Part

The shelf-life of the new hyperbaric compositions in accordance with the present invention, obtained with the method described herein, was determined as follows: In particular, for the following tests relating to batches 26102, 26103 and 26104, a solution was used consisting of 2% (w/V) of prilocaine HCl and 6% (w/V) of anhydrous glucose in water for injection without preservatives and/or stabilizers, to which NaOH was added, initially in small quantities, to balance the pH on achieving the initially envisaged window. The osmolarity of the new hyperbaric compositions tested herein was between 490 and 540 mOsm/kg.

Specifications of the hyperbaric 2% prilocaine product, 5 ml vials

| N° | Test | Method | Specification at t = 0 | Specification at end of shelf-life |
|---|---|---|---|---|
| 1 | Colour & transparency | Eur. Ph. | Clear and colourless | Clear and colourless |
| 2 | Prilocaine titre | HPLC method given in the Eur. Ph. monograph "Prilocaine Hydrochloride" | 95.0-105.0% | 95.0-105.0% |
| 3 | 2-methylaniline titre | HPLC method based on the method for determining o-Toluidine given in the Eur. Ph. monograph "Prilocaine Hydrochloride" | ≦0.10% (relative to prilocaine content) | ≦0.10% (relative to prilocaine content) |
| 4 | Glucose titre | Spectrophotometric method taken form "Swiss manual of foodstuffs" | 95.0-105.0% | 95.0-105.0% |
| 5 | Solution pH | Eur. Ph. | 5.0-6.0 | 4.0-6.0 |
| 6 | Sterility | Eur. Ph | Sterile | Sterile |
| 7 | LAL test | Eur. Ph | <0.25 IU/ml | <0.25 IU/ml |

Product: Hyperbaric 2.0% Prilocaine HCl Injection, 5 mL vials
Batch number: 26104
Storage conditions: 25° C. ± 2° C.
Date of manufacture: 31 Mar. 1999
Batch size: Industrial
Packaging: 5 mL clear vials, Type I glass It can also be noted that in the first two years, 2-methylaniline is not analytically detectable i.e. the quantity of 2-methylaniline possibly contained in the vials tested as above would remain under the limit of 0.0008% of 2-methylaniline relative to the prilocaine HCl content (a limit which corresponds to 0.162 µg/ml of 2-methylaniline on an absolute scale).

In this context, it is also important to note that the finally sterilized solutions proved to be perfectly clear and colourless

| Test | Specification | Time (months) | | | | |
|---|---|---|---|---|---|---|
| | | 0 | 3 | 6 | 9 | 12 |
| Solution appearance | Clear and colourless | Conforms | Conforms | Conforms | Conforms | Conforms |
| pH | 4.0-6.0 | 5.3 | 5.3 | 5.3 | n.d. | 5.3 |
| Titre Prilocaine HCl (%) | 95.0-105.0 | 99.8 | 98.5 | 100.5 | 98.0 | 99.4 |
| Titre Glucose (%) | 95.0-105.0 | 99.8 | 101.0 | 99.8 | 99.8 | 100.3 |
| 2-methylaniline (%) | ≦0.10 | <0.0008% (<0.162 µg/ml) | <0.0008% (<0.162 µg/ml) | <0.0008% (<0.162 µg/ml) | <0.0008% (<0.162 µg/ml) | <0.0008% (<0.162 µg/ml) |
| Sterility | sterile | Sterile | n.d. | n.d. | n.d. | n.d. |
| LAL Test | <0.25 IU//ml | <0.25 IU/ml | n.d. | n.d. | n.d. | n.d. |

| Test | Specification | Time (months) | | | | |
|---|---|---|---|---|---|---|
| | | 18 | 24 | 36 | 48 | 60 |
| Solution appearance | Clear and colourless | Conforms | Conforms | Conforms | Conforms | Conforms |
| pH | 4.0-6.0 | 5.1 | 5.0 | 5.0 | 4.7 | 4.7 |
| Titre Prilocaine HCl (%) | 95.0-105.0 | 101.8 | 98.0 | 100.3 | 100.0 | 99.5 |
| Titre Glucose (%) | 95.0-105.0 | 100.7 | 100.1 | 100.9 | 102.0 | 101.0 |
| 2-methylaniline (%) | ≦0.10 | <0.0008% (<0.162 µg/ml) | <0.0008% (<0.162 µg/ml) | 0.059% | 0.03% | <0.0008% (<0.162 µg/ml) |
| Sterility | sterile | n.d. | n.d. | n.d. | n.d. | Sterile |
| LAL Test | <0.25 IU//ml | n.d. | n.d. | n.d. | n.d. | <0.25 IU/ml |

(0.162 µg/ml corresponds to detection limit for 2-methylaniline). The LAL test and sterility are repeated only at the end of shelf-life (60 months).

From the aforesaid results it can be deduced that the shelf-life of the new hyperbaric prilocaine HCl compositions is at least 5 years, since throughout the entire period of observation, the 2-methylaniline limit of 0.10% relative to the prilocaine HCl content, a limit that is considered unacceptable in prilocaine preparations according to European Pharmacopeia 5.0 monograph 1363, is never attained. In particular, 0.060% of 2-methylaniline relative to the prilocaine HCl content, are never exceeded throughout the entire 5 year span.

throughout the entire shelf-life span (5 years), i.e. without the slightest formation of precipitates and/or the development of colouration.

Similar results were obtained with the other batches 26102 and 26103, tested under identical conditions to those specified above.

It has therefore been demonstrated how the new stable hyperbaric solutions described herein resolve the identified technical problem.

CITED LITERATURE

1). Rigler M L., Drasner K., Krejcle T C. et. Al. Cauda equina syndrome after continuous spinal anesthesia. Aesth. Analg. 1991; 72:275-81.
2). Drasner K. Rigler M L. Repeat injection after a "failed spinal": At times, a potentially unsafe practice. Anesthesiology 1991; 75:713-4.
3). Gerancher J C. Cauda equina syndrome following a single spinal administration of 5% hyperbaric lidocaine through a 25-gauge Whitacre needle. Anesthesiology 1997; 87:687-9.
4). Hodgson, P S, Liu S S, Batra M S et al. Procaine compared with lidocaine for incidence of transient neurologic symptoms. Reg. Anesth. Pain Med, 2000; 25: 218-22.
5). Crankshaw, T P. Citanest® (Prilocaine) in spinal analgesia. Acta anaesth. Scandinav. 1965, Suppl. XVI, 287-290.
6). Fisher A., Bryce-Smith R. Spinal analgesic agents: A comparison of cinchocaine, lignocaine and prilocaine. Anaesthesia Vol. 26 No. 3, 1971.
7). Hillmann K M, Spinal prilocaine. Anaesthesia 33:68-9, 1978.
8). Robertson D H, Spinal prilocaine. Anastesia 33: 647-8, 1978.
9). Gleizal B et al., Effects of increased doses of adrenaline on the duration of spinal anaesthesia with prilocaine. Ann. Fr. Anesth. Reanim 8: Suppl. R 165, 1989.
10). Tauzin-Fin P. et al., Combination pethidine-prilocaine in spinal anesthesia. Clinical and pharmacokinetic aspects. Ann. Fr. Anesth. Reanim 8: Suppl. R 148, 1989.
11). Mora C, Dupuis J L and Feiss P. Spinal anesthesia and Morphine analgesia in prostatic surgery. Cah. Anaesthesiol. 33:25-7, 1985.
12). Brun-Buisson V. et al. Failure of spinal anesthesia. Evaluation of the practice at a university hospital. Ann Fr. Anesth. Reanim. 7:383-6, 1988.
13). König W., Ruzizic, D. Absence of transient radicular irritation after 5000 spinal anesthetics with prilocaine. Anesthesia 52:182-3, 1997.
14). Hampl K F. et al. Transient neurologic symptoms after spinal anesthesia: A lower incidence with prilocaine and bupivacaine than with lidocaine.
15). De Weert K. et al. The incidence of transient neurological symptoms after spinal anesthesia with lidocaine compared to prilocaine. Anaesthesia 55: 1003-24, 2000.
16). Ostgaard et al. A randomized study of lidocaine and prilocaine for spinal anaesthesia. Acta Anaesthesiol. Scad. 44:436-450, 2000.
17). Eberhardt et al. Transiente neurologische Symptome nach Spinalanasthesie. Anesthesist 51:539-46, 2002.

The invention claimed is:

1. A pharmaceutical composition, which is stable and has a shelf-life, at ambient temperature, of at least 5 years, wherein the composition comprises prilocaine HCl and glucose in a hyperbaric solution of water for injection and has a 2-methylaniline content, throughout the entire shelf-life duration, of less than 0.10% relative to the quantity of prilocaine HCl contained,
   wherein the prilocaine HCl content is from 1.8% to 2.2% (w/V), the glucose content, expressed as anhydrous glucose, is from 5.4% to 6.6% (w/V) and the osmolarity is in the range from 490 to 540 mOsm/kg.

2. The pharmaceutical composition according to claim 1, wherein said composition is free of stabilizers and/or preservatives.

3. The pharmaceutical composition according to claim 1, wherein the prilocaine HCl content is 2% (w/V).

4. The pharmaceutical composition according to claim 1, wherein the 2-methylaniline content, throughout the entire shelf-life duration, is less than 0.060% relative to the quantity of prilocaine HCl contained.

5. The pharmaceutical composition according to claim 1, having a relative density at 37° C. of between 1.0210 and 1.0310.

6. The pharmaceutical composition according to claim 1, having a pH between 5.0 and 6.0.

7. An injectable solution for intrathecal anaesthesia consisting of a composition according to claim 1.

8. A vial of clear or dark glass containing the solution claimed in claim 7.

* * * * *